(12) United States Patent
Sohn

(10) Patent No.: US 10,772,713 B2
(45) Date of Patent: Sep. 15, 2020

(54) VIBRATING TOOTHBRUSH

(71) Applicant: One Star International Co., Ltd., Incheon (KR)

(72) Inventor: Jae Hoon Sohn, Incheon (KR)

(73) Assignee: ONE STAR INTERNATIONAL CO., LTD., Incheon (KR)

( * ) Notice: Subject to any disclaimer, the term of this patent is extended or adjusted under 35 U.S.C. 154(b) by 36 days.

(21) Appl. No.: 16/198,206

(22) Filed: Nov. 21, 2018

(65) Prior Publication Data

US 2020/0138555 A1    May 7, 2020

(30) Foreign Application Priority Data

Nov. 7, 2018   (KR) .................. 10-2018-0135700

(51) Int. Cl.
| | | |
|---|---|---|
| A61C 17/22 | (2006.01) | |
| A46B 13/00 | (2006.01) | |
| A46B 13/02 | (2006.01) | |
| A46B 15/00 | (2006.01) | |
| A46B 17/04 | (2006.01) | |
| A46B 17/06 | (2006.01) | |
| A46B 5/00 | (2006.01) | |
| A61C 17/34 | (2006.01) | |
| A61L 2/10 | (2006.01) | |

(Continued)

(52) U.S. Cl.
CPC .......... *A61C 17/221* (2013.01); *A46B 5/0095* (2013.01); *A46B 13/003* (2013.01); *A46B 13/023* (2013.01); *A46B 15/004* (2013.01); *A46B 15/0008* (2013.01); *A46B 15/0044* (2013.01); *A46B 15/0046* (2013.01); *A46B 17/04* (2013.01); *A46B 17/065* (2013.01); *A61C 17/3481* (2013.01); *A61L 2/10* (2013.01); *F21V 23/003* (2013.01); *G08B 7/06* (2013.01); *A46B 5/023* (2013.01); *A46B 15/0089* (2013.01); *A46B 2200/1066* (2013.01); *F21W 2111/00* (2013.01)

(58) Field of Classification Search
CPC . A61C 17/221; A61C 17/3481; A46B 5/0095; A46B 13/003; A46B 13/023; A46B 15/0008; A46B 15/004; A46B 15/0044; A46B 15/0046; A46B 17/04; A46B 17/065; A61L 2/10; F21V 23/003; G08B 7/06

See application file for complete search history.

(56) References Cited

U.S. PATENT DOCUMENTS

| | | | | |
|---|---|---|---|---|
| 2,599,019 A | * | 6/1952 | Rupert ................ | A45D 44/18 132/289 |
| 2003/0031979 A1 | * | 2/2003 | Shortt .................. | A61C 17/22 433/118 |

(Continued)

FOREIGN PATENT DOCUMENTS

| | | |
|---|---|---|
| KR | 10-2013-0021158 A | 3/2013 |
| KR | 10-2015-0011951 A | 2/2015 |

*Primary Examiner* — Shay Karls
(74) *Attorney, Agent, or Firm* — Stein IP, LLC

(57) ABSTRACT

The present invention relates to a vibrating toothbrush, and more particularly to a vibrating toothbrush enabled to perform toothbrushing for a running time, periodically output an alarm signal in a multisensory way to guide change of a region subject to toothbrushing, and supply driving power in the form of pulses according to a period, thereby reducing power consumption and rapid driving stress of a motor.

8 Claims, 7 Drawing Sheets

(51) Int. Cl.
*F21V 23/00* (2015.01)
*G08B 7/06* (2006.01)
*F21W 111/00* (2006.01)
*A46B 5/02* (2006.01)

(56) References Cited

U.S. PATENT DOCUMENTS

2006/0037158 A1\* 2/2006 Foley .................... A46B 9/026
 15/105
2008/0196185 A1\* 8/2008 Gatzemeyer ....... A46B 15/0002
 15/23
2018/0132604 A1\* 5/2018 Gatzemeyer ....... A46B 15/0044

\* cited by examiner

VIBRATING TOOTHBRUSH

CROSS-REFERENCE TO RELATED APPLICATIONS

This application claims the benefit of Korean Application No. 10-2018-0135700, filed Nov. 7, 2018, in the Korean Intellectual Property Office. All disclosures of the document named above are incorporated herein by reference.

BACKGROUND OF THE INVENTION

Field of the Invention

The present invention relates to a vibrating toothbrush, and more particularly to a vibrating toothbrush enabled to perform toothbrushing for a running time, periodically output an alarm signal in a multisensory way to guide change of a toothbrushing region, and supply driving power in the form of pulses according to a period, thereby reducing power consumption and rapid driving stress of a motor.

Related Art

Generally, a toothbrush is used to clean teeth and gums with toothpaste which is supposed to go atop of bristles. The toothbrush is not just to clean the teeth, but also touches the gums to help blood circulation, thereby improving gums health and preventing periodontal diseases.

Such a toothbrush consists of a plastic handle and a bristles. This kind of manual toothbrush is used to remove food residues or plaque existing in teeth by use of movement of a user's wrist or arm.

Recently, vibrating toothbrushes have developed, which automatically moves bristles by electric power in order to brush teeth. Existing technologies relating to a vibrating toothbrush and toothbrush sterilization include, for example, Korean Patent Application Publication No. 10-2015-0011951 (Document 1) and Korean Patent Application Publication No. 10-2013-0021158 (Document 2).

Document 1 relates to an electric toothbrush 10 having a toothbrushing guide function, including: a supporting body 100 supporting and protecting power elements, a power supply, etc.; three types of buttons 110 of red 111, yellow 112, and green 113 with functions of adjusting the power or the like of the electric toothbrush 10; a speaker 120 outputting guide voice of toothbrushing; a timer 130 displaying operating time and remaining time; an opening and closing cover 140 protecting a battery; a rubber support 150 preventing the electric toothbrush 10 from being dropped and giving comfortable feeling to a user, a toothbrush joint 160 serving as a supporting role and supplying power; a toothbrush body 200 supporting cleaning elements and transferring power; a toothbrush head 210 cleaning the mouth and having a vibrating function; and an electric groove 220 supplying power to the toothbrush body 200 when being connected with the toothbrush joint 160.

Existing vibrating toothbrushes including Document 1 are apparatuses that move bristles by rotation of a motor. If a rotational force is too strong, the existing vibrating toothbrushes may hurt teeth or gums. In addition, since the existing vibrating toothbrushes rotate bristles in a predetermined direction, there is a limitation in cleaning the teeth.

In addition, during a running time of toothbrushing by an electric power, a motor keeps operating, thereby leading to a considerable amount of power consumption. At a time when the motor operates upon a supply of power, a significant amount of currents, that is, initial driving currents of the motor is consumed, thereby reducing a usage time of the battery.

In addition, since a user is not able to check or be aware of the best toothbrushing time when using the existing electric toothbrushes (including manual toothbrushes), the user has to rely on senses when brushing his/her teeth. This is a limit to the best toothbrushing. In addition, there is another problem that each region of teeth is not brushed equally for a predetermined period of time.

In addition, if the existing vibrating toothbrushes are not sterilized after toothbrushing, germs may thrive in the toothbrush, causing a concern about the unsanitary condition.

Meanwhile, Document 2 relates to a toothbrush cap with an ultraviolet (UV) sterilization function, including: a toothbrush lid cover 210 on which a battery 212, a controller 213, a switch 214, and a UV lamp 215 are installed; and a toothbrush lid body 201 having a rubber part 202 attachable to a glass. The toothbrush lid cover 210 is connected to a lid opening and closing shaft 203 provided on one side of the toothbrush lid body 201. A switch 214 is configured to operate when the toothbrush lid cover 210 is covered by the toothbrush lid body 201. Power from the battery 212 provided in the toothbrush lid cover 210 causes the UV lamp 215, provided on the toothbrush lid cover 210, to be turned on for a predetermined period of time, thereby sterilizing bristles 203 in a simple way.

Document 2 relates to a UV sterilizing toothbrush lid which is mounted over bristles after toothbrushing to sterilize the bristles for a predetermined period of time. Document 2 is a technology capable of solving the unsanitary problem of the existing electric toothbrushes (including manual toothbrushes) including Document 1.

However, since Document 2 has a structure in which the toothbrush lid cover 210 is opened and closed with reference to the toothbrush lid body 201, the UV sterilizing toothbrush according to Document 2 would be left on a wash basin during toothbrushing and thus can be lost easily. In addition, electrical error may frequently occur when water flow to the inside of an electric circuit or the UV lamp.

Examples of the related arts relating to a vibrating toothbrush and toothbrush sterilization are as follows.

Document 1: Korean Patent Application Publication No. 10-2015-0011951 (Title: ELECTRIC TOOTHBRUSHING HAVING TOOTHBRUSHING GUIDE FUNCTION; Filing Date: Jul. 24, 2013)

Document 2: Korean Patent Application Publication No. 10-2013-0021158 (Title: ULTRAVIOLET STERILIZING TOOTHBRUSH LID; Filing Date: Aug. 22, 2011)

SUMMARY OF THE INVENTION

In order to solve the above drawbacks, the present invention provides a vibrating toothbrush, and more particularly to a vibrating toothbrush enabled to perform toothbrushing for a running time, periodically output an alarm signal to guide change of a toothbrushing region, and supply driving power in the form of pulses according to a period, thereby reducing power consumption and rapid driving stress of a motor.

In one general aspect of the present invention, there is provided a vibrating toothbrush including: a body defining a handle; a vibration generator embedded in the body and configured to generate a vibrating force; a light source unit embedded in an end portion on one side of the body and configured to generate light; a shaft detachably fixed to the end portion on one side of the body configured to guide and emit the generated light to an outside and transfer the generated vibrating force to bristles provided on the end portion on one side of the body; and a controller provided in the body and configured to perform control to conduct or block power from a power unit to a light source to the vibration generator at every preset cycle during a running time and block power at an operation end point.

An exterior of the body may be covered by a water-proof outer cover.

The vibrating toothbrush may further include a sound output unit configured to output sound for an alarming operation time at every preset cycle under control of the controller until a running time expires.

A running time of the controller may be 2 to 3 minutes from an operation start point to the operation end point, the preset cycle may be 30 seconds which is a sum of a main toothbrushing time of 28 seconds for actually performing toothbrushing and an alarming operation time of 2 seconds for notifying a time to change a toothbrushing region, and a time interval identical to a time interval for the alarming operation may be applied to an initial operation start point.

The controller may be further configured to conduct power to the vibration generator and the light source unit until expiration of the running time in an manner in which the power is blocked with respect to the vibration generator and the power source unit during an alarming operation time from expiration of each preset cycle and the power is conducted upon expiration of the alarming operation time or in an manner in which the power is conducted to the sound output unit for an alarming operation time and then blocked upon expiration of the alarming operation.

The controller may be further configured to: at an operation start point, conduct the power to the vibration generator and the light source by immediately increasing a level of the power, gradually increasing the level of the power for a predetermined time, or alternatively supplying the power in a pulse form; at a point of arrival of an alarming operation time upon expiration of each preset cycle, block the power by immediately decreasing the level of the power and, when the alarming operation time expires, conduct the power by the level of the power, gradually increasing the level of the power for the alarming operation time, or alternatively supplying the power in a pulse form; and, at the operation end point, block the power by immediately decreasing the level of the power.

The vibrating toothbrush may further include a block cap which is, when used, fitted to one side end of the body to extend the length of the handle, and, when not used, fitted to the other side end of the body to block the shaft and the bristles from the outside, and the block cap may include a sterilizer provided inside an end portion thereof and configured to, upon the fitting of the block cap to the body, be turned on simultaneously, thereby sterilizing a portion around the bristles.

DESCRIPTION OF EXEMPLARY EMBODIMENTS

Hereinafter, the present invention will be described with reference to the accompanying drawings.

Figure 1:
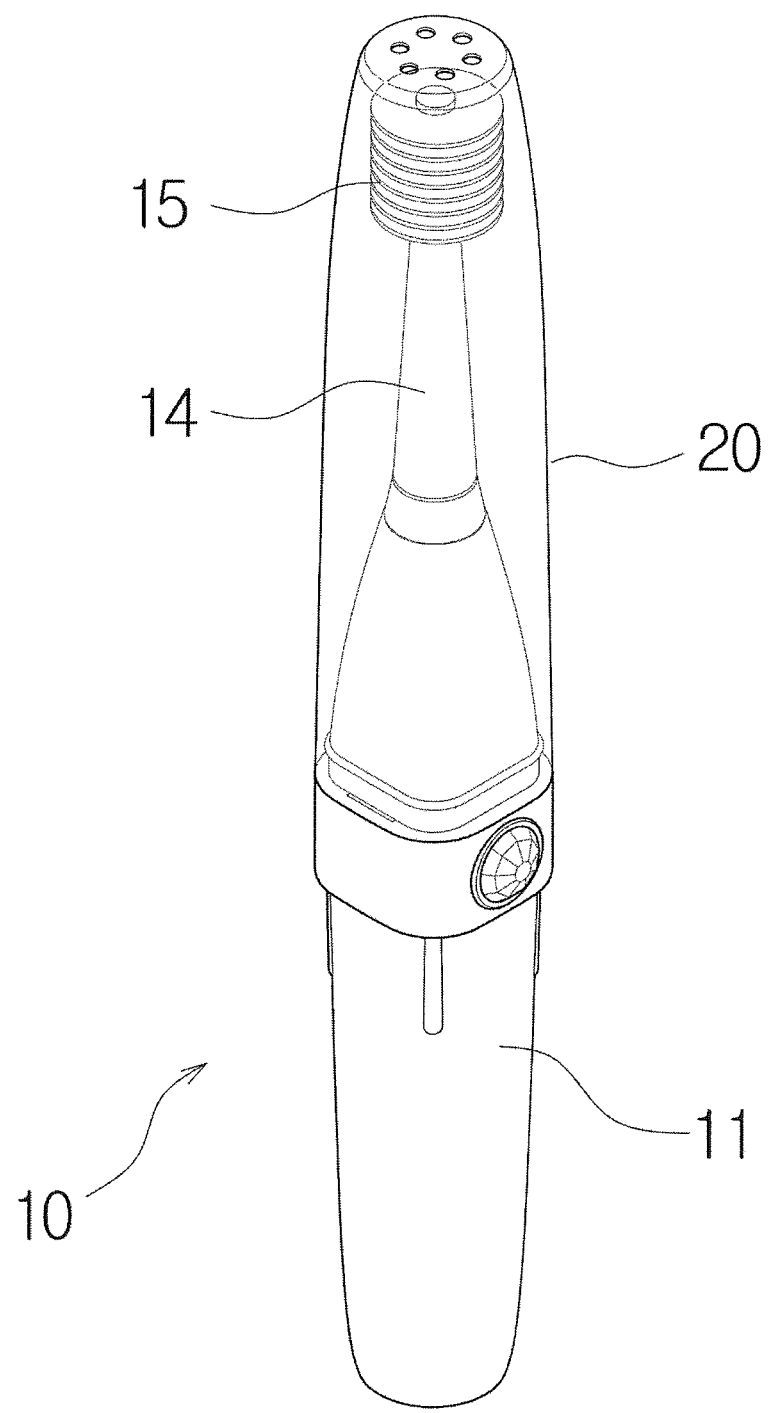
FIG. 1 is a perspective view of exterior configurations of the present invention.
Figure 2:
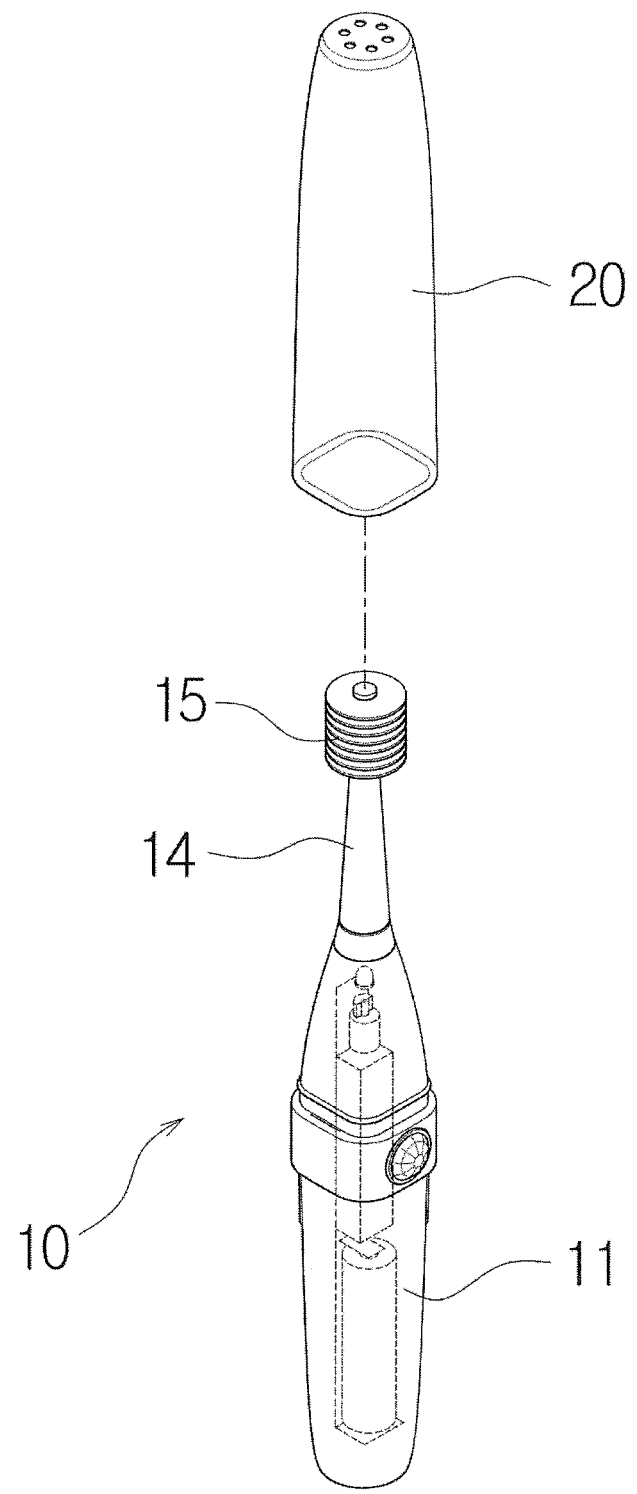
FIG. 2 is a perspective view illustrating detailed exterior and interior configurations of the present invention.

As illustrated in FIGS. 1 and 2, a vibrating toothbrush 10 according to the present invention may include: a body 11 defining a handle; a vibration generator 12 embedded in the body 11 to generate a vibrating force; a light source unit 13 embedded in an end portion on one side of the body 11 to generate light; a shaft 14 detachably fixed to the end portion on one side of the body 11 to guide the generated light to an outside and transfer the generated vibrating force to bristles 15 provided at the end portion; and a controller 16 provided in the body 11 to conduct/block power from a power unit 17 to the vibration generator 12 and the light source unit 13 at a preset cycle during a running time and block power at an operation stop time.

Figure 3:
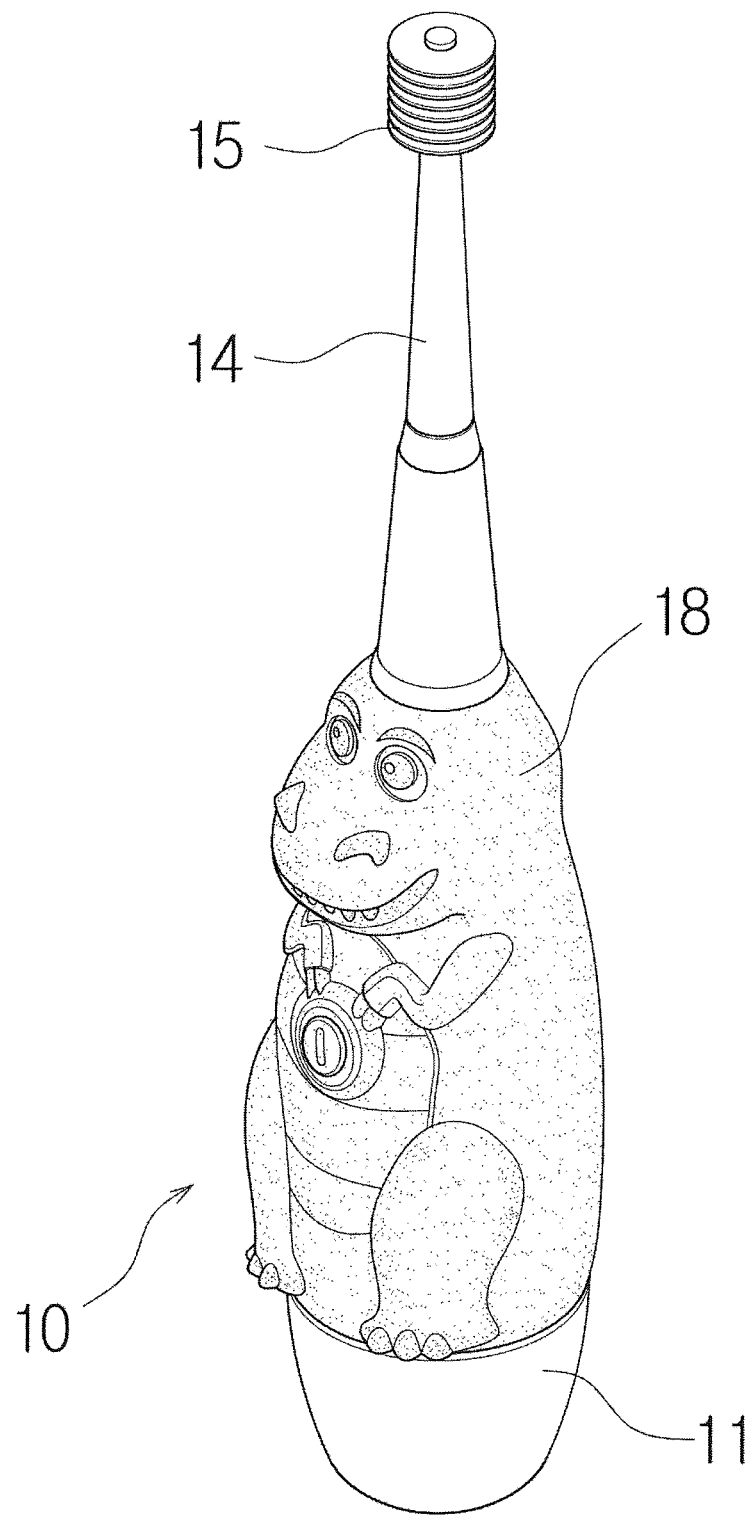
FIG. 3 is a perspective view of an example in which an outer cover is applied to a body of the present invention.

In addition, as illustrated in FIG. 3, the exterior of the body 11 may be further covered by a water-proof outer cover 18. According to an embodiment, the outer cover 18 may be a character cover made of a silicon material.

In addition, the body 11 may further include a sound output unit 19 that outputs sound at every preset cycle under control of the controller until a running time expires.

The vibration generator 12 may be an ultrasonic vibration generator including an eccentric motor. According to an embodiment, the vibration generator 12 may be a motor.

The vibration generator 12 may be provided in proximity to a portion of the body 11 in which the light source unit 13 is embedded.

In this case, the vibration generator 12 may be provided on a straight line with the shaft 14 or may be provided at a position at a position not on the straight line with the shaft 14.

In the case where the vibration generator 12 is provided on the straight line with the shaft 14, the vibration generator 12 may be provided at a position relatively far from the shaft 14 than the light source unit 13 is. In the case where the vibration generator 12 is provided at a position not on the straight line with the shaft 14, the vibration generator 12 may be provided adjacent to one side of the light source unit 13.

Meanwhile, the light source unit 13 may be a light generator including a light emitting device (LED). According to an embodiment, the light source unit 13 may be an LED.

The light source unit 13 may be provided inside a groove at an end portion on one side of the body 11, the end portion from which the shaft 14 is detachable.

In this case, the light source unit 13 is preferably provided in proximity to the shaft 14 rather than at least the vibration generator 12.

In addition, the bristles 15 may be highly elastic microfibers which are provided at an end portion of the shaft 14 in multiple layers along a lengthwise direction in all directions of 360 degrees.

The bristles 15 may be implanted at the end portion of the shaft 14, or a head with the bristles implanted thereon may be detachably fixed to an end portion of the shaft 14.

In addition, the controller 16 may include a control circuit embedded in the body 11 and a manipulation switch exposed to an outside of the body 11.

A running time of the controller 16 may be set to 2 to 3 minutes from an operation start point to an operation end point. A preset cycle may be 30 seconds which is a sum of the main toothbrushing time of 28 seconds for actually performing toothbrushing and an alarming operation time of 2 seconds for informing a time to change a toothbrushing region. An interval identical to the alarming operation time may be applied to an initial operation start time.

The controller 16 conducts power to the vibration generator 12 and the light source unit 13 until expiration of the running time in a manner in which the power is blocked to the vibration generator 12 and the light source unit 13 upon expiration of each preset cycle for an alarming operation time and then the power is conducted upon the expiration of the alarming operation time, or in a manner in which the power is conducted to the sound output unit 19 for an alarming operation time and then blocked upon expiration of the alarming operation time.

In this case, at the operation start point, the controller 16 may conduct the power to the vibration generator 12 and the light source 13 by immediately increasing a level of the power, gradually increasing the level of the power for a predetermined period of time (identical to the alarming operation time), or alternatively supplying the power in the form of pulses. At a point of arrival of an alarming operation time upon expiration of each preset cycle, the controller 16 may block the power by immediately decreasing the level of the power and, when the alarming operation time expires, conduct the power by the level of the power, gradually increasing the level of the power for the alarming operation time, or alternatively supplying the power in the form of pulses. At an operation end point, the controller 16 may block the power by immediately decreasing the level of the power.

Following is description about operations of the present invention.

As illustrated in FIGS. 1 and 2, the present invention relates to the vibrating toothbrush 10 according to the present invention may include: the body 11 defining a handle; the vibration generator 12 embedded in the body 11 to generate a vibrating force; the light source unit 13 embedded in an end portion on one side of the body 11 to generate light; the shaft 14 detachably fixed to the end portion on one side of the body 11 to guide the generated light to an outside and transfer the generated vibrating force to the bristles 15 provided at the end portion on one side of the body 11; and the controller 16 provided in the body 11 to conduct/block power from a power unit 17 to the vibration generator 12 and the light source unit 13 at a preset cycle for a preset time and block power at an operation end point.

In addition, as illustrated in FIG. 3, the exterior of the body 11 is preferably covered by a character outer cover 18 made of silicon. In this case, the exterior of the body 11 may be covered by using any of various character outer covers 18, and therefore, a variety of aesthetic appearance may be realized. Also, the outer cover 18 provides a better sense of gripping when a user grips the body 11, and prevents the outer cover 18 from being slipped from the user's hand. In addition, the outer cover 18 prevents vibration generated in the vibration generator 12 from being delivered to the user's hand. Furthermore, the outer cover 18 minimizes the possibility of the vibrating force to be lost in the hand, and transfers the vibrating force to the bristles 15 through the shaft. Moreover, the outer cover 18 prevents water from flowing into the inside.

In addition, the body 11 preferably further includes a sound output unit 19 that outputs sound at a preset cycle under control of the controller until a running time expires. In this case, it is possible to notify a time to change a toothbrushing region in a multisensory way by means of sound output in addition to change in vibration generated by the vibration generator 12 and/or turning-on/off op of light generated by the light source unit 13.

The vibration generator 12 is an ultrasonic vibration generator including an eccentric motor. According to an embodiment, a motor may be the vibration generator 12. In this case, the motor generates vibration by eccentrically rotating at 8000-9000 rpm (preferably 8000 rpm).

The vibration generator 12 is preferably provided in proximity to a portion of the body 11 in which the light source unit 13 is embedded. In this case, a next stage adjacent directly to the light source unit 13 transferring light directly to the shaft 14 is allowed to transfer a vibrating force to the shaft 14 with the maximum proximity to the light source unit 13.

In this case, the vibration generator 12 is preferably provided on a straight line with the shaft 14, and the vibration generator 12 may be provided at a position not on the straight line with the shaft 14. When the vibration generator 12 is provided with a straight line with the shaft 14, a vibrating force is transferred primarily to the shaft 14, thereby maximizing the vibrating force. When the vibration generator 12 is provided at a position not on the straight line with the shaft 14, vibration is transferred while the vibrating force is reduced but a wavelength width expands as much as a distance from the central axis of the shaft 14.

Meanwhile, the light source unit 13 is a light generator including an LED. According to an embodiment, an LED module is applied. The light source unit 13 is provided inside a groove at an end portion on one side of the body 11 from which the shaft 14 is detachable, such that generated light is introduced through one side end of the shaft 14 without a loss and guided to emit light to the outside.

In addition, the bristles 15 may be highly elastic microfibers which are provided at an end portion of the shaft 14 in multiple layers along a lengthwise direction in all directions of 360 degrees. In this case, a circular shape provided in all directions of 360 degrees is capable of cleaning upper teeth and lower teeth at the same time with vibration and also capable of brushing the teeth to the left and to the right by itself.

The bristles 15 is preferably implanted at an end portion of the shaft 14, and a head with the bristles implanted thereon is also preferably fixed to the front end of the shaft 14 in a detachable manner. In this case, when the bristles 15 are worn out, the bristles 15 may be separated from the shaft 14 for replacement.

In addition, the controller 16 includes a control circuit embedded in the body 11, and a manipulation switch exposed to an outside of the body 11. The control circuit of the controller 16 may be a Micom or a logic circuit in which a program for conducting/blocking power from the power unit 17 is set in advance, or a discrete circuit including a Micom and a logic circuit. The manipulation switch of the controller 16 may include a power switch for conducting/blocking power from the power unit 17 to the control circuit, or a group of setting switches for setting the running time, adjusting a level of the power, or selecting operations of the light source unit 13 and the sound output unit 19.

Figure 4:
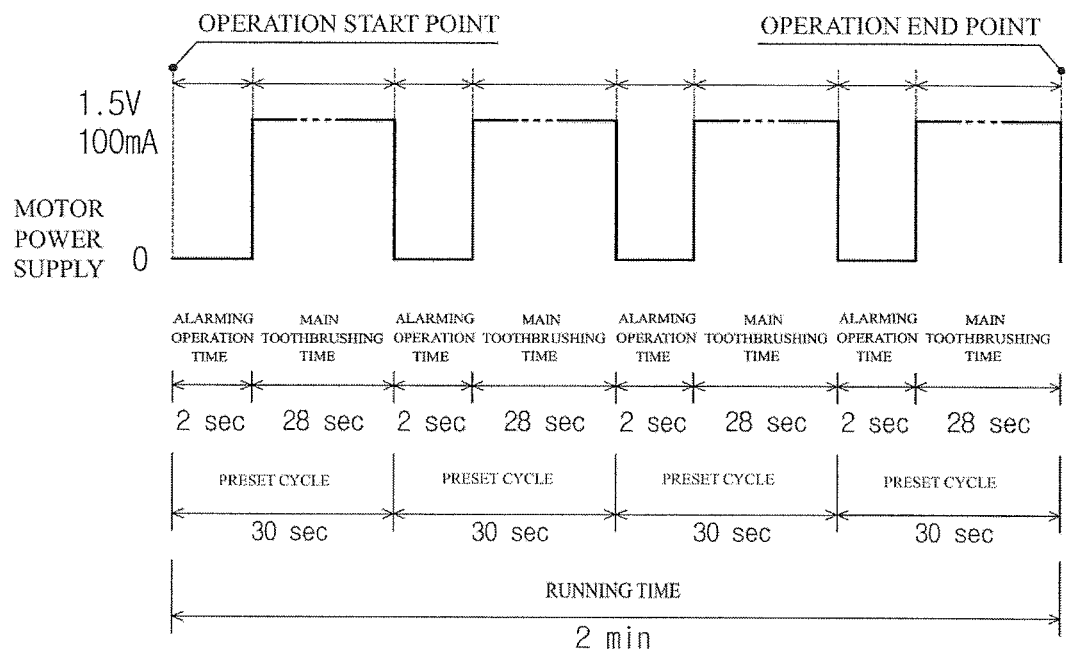
FIG. 4 is a waveform view illustrating an example of controlling driving power of a vibrating generator of the present invention.
Figure 5:
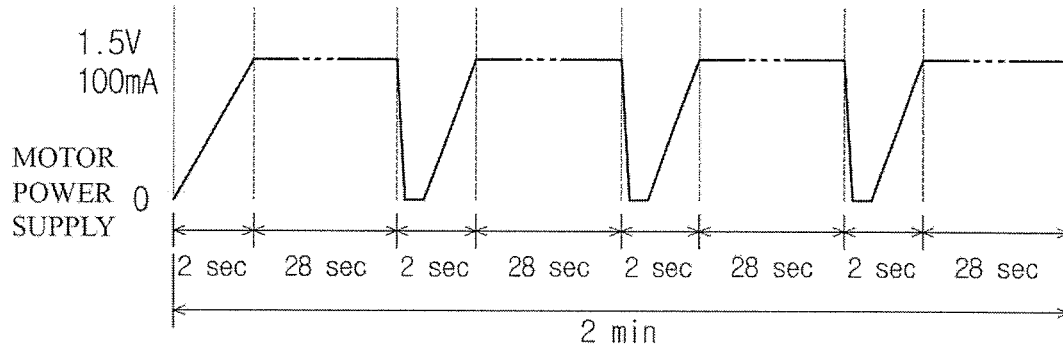
FIG. 5 is a waveform view illustrating another example of controlling driving power of a vibrating generator of the present invention.

In this case, a running time of the controller 16 may be set to 2 to 3 minutes from the operation state point to the operation end point, as illustrated in FIG. 4. A preset cycle is 30 seconds which is a sum of a main toothbrushing time of 28 seconds for actually performing toothbrushing and an alarming operation time of 2 seconds for notifying a time to change a toothbrushing region. An interval identical to the alarming operation time may be applied to an initial operation start point. The above-mentioned times may be increased or decreased according to pre-setting by a user.

In this case, the controller 16 conducts power to the vibration generator 12 and the light source unit 13 until expiration of the running time in a manner in which the power is blocked to the vibration generator 12 and the light source unit 13 upon expiration of each preset cycle for an alarming operation time and then the power is conducts the power upon the expiration of the alarming operation time, or in a manner in which the power is conducted to the sound output unit 19 for an alarming operation time and then blocked upon expiration of the alarming operation time.

Figure 6:
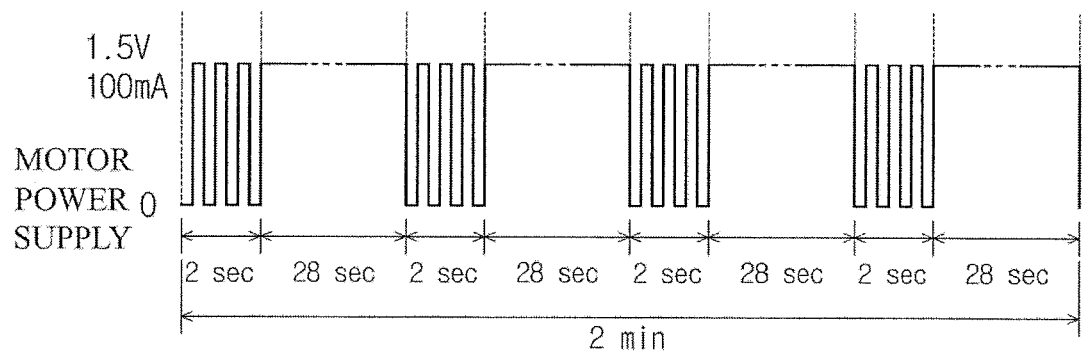
FIG. 6 is a waveform view illustrating yet another example of controlling driving power of a vibrating generator of the present invention.

More specifically, at the operation start point or at a point when an operation start notifying signal period (2 seconds) expires, as illustrated in FIG. 4, the controller 16 conducts power to the vibration generator 12 and the light source unit 13 by immediately increasing a level of the power, gradually increasing the level of the power for a predetermined time (identical to the alarming operation time), or alternatively supplying the power in the form of pulses, as illustrated in FIG. 6.

In addition, at a point when each preset cycle expires, that is, a point when the alarming operation time starts, the controller 16 conducts power by immediately decreasing a level of the power, as illustrated in FIG. 4. Then, when the alarming operation time expires, the controller conducts the power by immediately increasing the level of the power, gradually increasing the level of the power for the alarming operation time, or alternatively supplying the power in the form of pulses, as illustrated in FIG. 6. At an operation end point, the controller 16 blocks the power by immediately decreasing the level of the power.

According to the present invention, the running time which is an overall toothbrushing time may be set to 2 minutes, and the running time may be divided into preset cycles each of 30 seconds to change a toothbrushing region. In this case, each preset cycle of 30 seconds is divided into a main toothbrushing time of 28 seconds for actually performing toothbrushing and an alarming operation time of 2 seconds for notifying a time to change a toothbrushing region. These times may be increased or decreased according to pre-settings by a user.

In the 2-second section for notifying a time to change a toothbrushing region, currents are applied alternatively in the form of pulses, as described above. The period of this section may be any cycle between 0.1 to 0.6 seconds or may be changed within this range.

For example, the running time may be increased from 2 minutes to 3 or 4 minutes, and each preset cycle may be increased from 30 seconds to 45 seconds including a main toothbrushing time of 42 seconds and an alarming operation time of 3 seconds. These settings may be changed through manipulation of the controller 16 by a user, when necessary.

In this case, at a point when the main toothbrushing time expires and the alarming operation time starts, tactile alarming is be possible through change in vibration generated by a motor, which is the vibration generator 12, and visible alarming is possible through change of a turn-on color or blinking of an LED module which is the light source unit 13, and, in addition, audible alarming is possible through alarming of a buzzer which is the sound output unit 19. As such, the present invention may integratedly or selectively provide various alarming modes to a user.

According to the present invention, the vibrating toothbrush 10 may be used with low power consumption using a 30-second alarming function for notifying a time to change of a toothbrushing region. For example, as driving power is supplied to the vibration generator 12 and/or the light source unit 13 for an alarming operation time, it is possible to prevent that a great amount of currents are consumed instantly upon driving of the motor. In addition, as driving currents are not supplied constantly, it is possible to minimize the amount of current consumption, thereby enabling low power-consumption operation compared to the case of supplying currents constantly.

Figure 7:
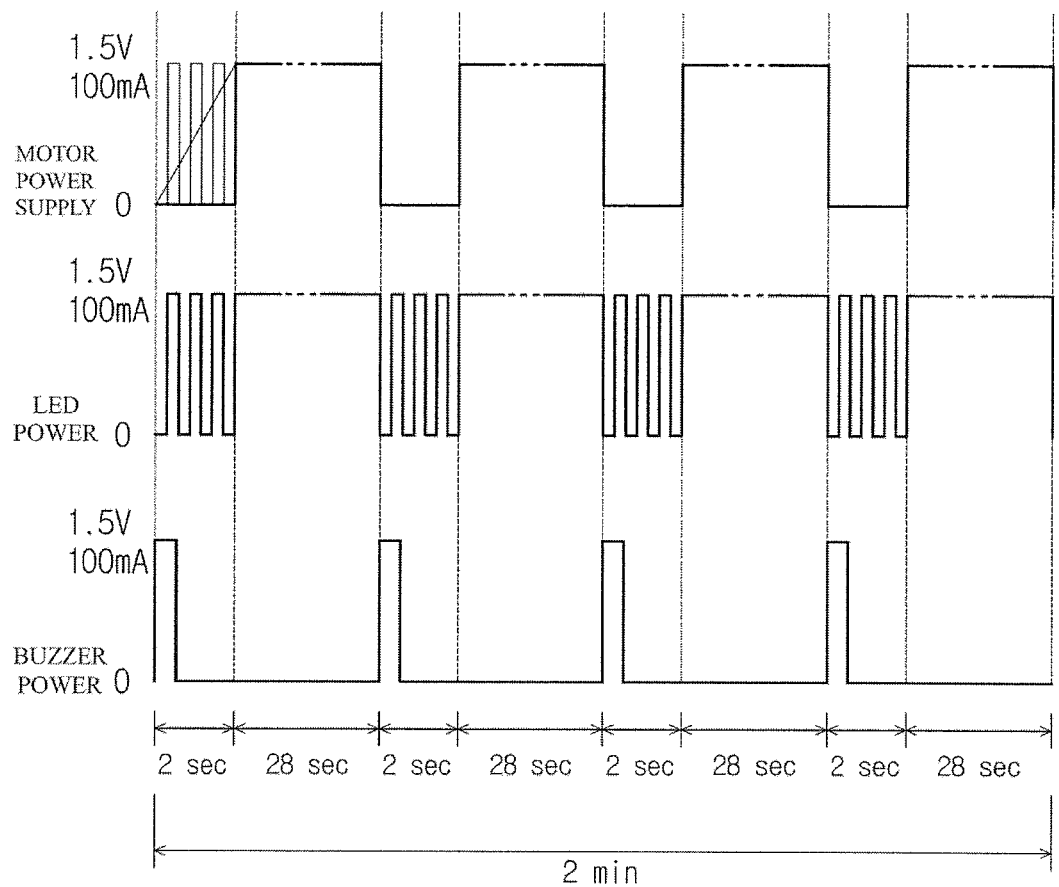
FIG. 7 is a waveform view of an example of overall controlling a vibration generator, a light source unit, and a buzzer of the present invention.
Figure 8:
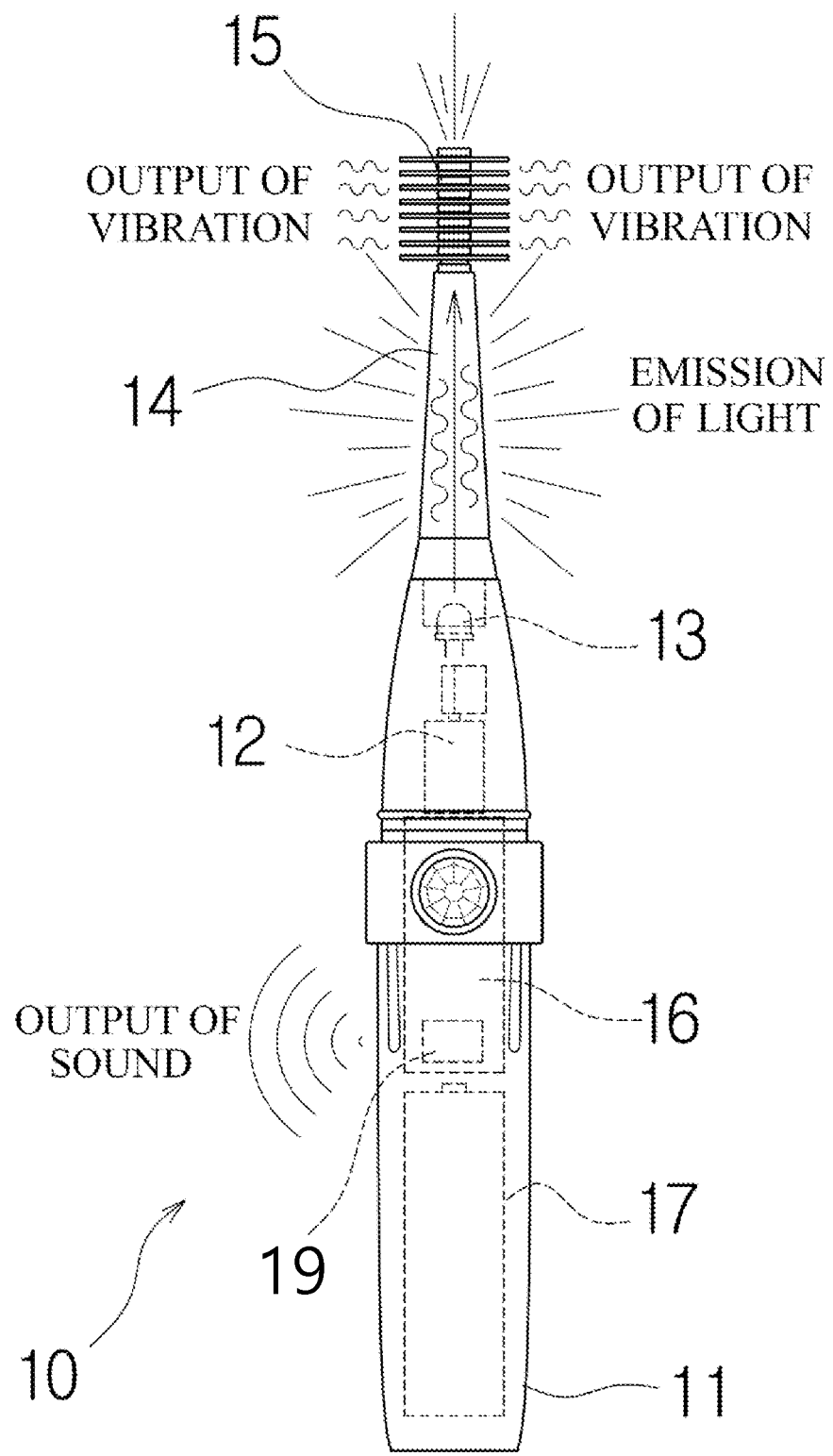
FIG. 8 is a front view illustrating an operating state of the present invention.

The present invention has conditions that a battery of the present invention is 1200 mAh/consumption currents (100 mA×12 h) and that toothbrushing is performed two times a day for 2 minutes each time. Under these conditions, following is description about how to realize low power consumption by controlling driving currents in the form of pulses in 50% duty cycle (see FIGS. 4 and 7) for a 2-second alarming operation in the a 30-second preset cycle during a 2-minute running time. Of course, the following example is merely to provide a better understanding with numerical values, and aspects of the present invention are not limited thereto.

With the battery under the above conditions, an available use time of a vibrating toothbrush is calculated as follows.

2 Minutes/One Time×2 Times=4 Minutes/One Day

Four Minutes×30 Days=120 Minutes (2 Hours)

120 Minutes×6 Months=720 Minutes (120 Hours)

This means that the vibrating toothbrush can be used for 12 hours with one battery.

Considering the above, if driving currents are controlled in the form of pulses in 50% duty cycle for a 2-second alarming operation time in a 30-second preset cycle during a 2-minute running time from an operation start point to an operation end point, the following results may be achieved.

A current consumption time may be reduced by 8 seconds each time.

A current consumption time may be reduced by 16 seconds a day since the vibrating toothbrush is used two times a day.

A current consumption time may be reduced by 480 seconds for 30 days (one month).

A current consumption time may be reduced by 2,880 seconds, that is, 48 minutes, for 180 days (6 months).

This means that a current consumption time can be reduced by 48 minutes for sixth months (720 mins) which is available usage time of one battery.

As such, the usage time of one battery may be reduced by 48 minutes out of 720 minutes, thereby reducing the entire consumption time by 6.6% and accordingly reducing the power consumption by 6.6%. This means that toothbrushing can be performed 24 times more.

Figure 9:
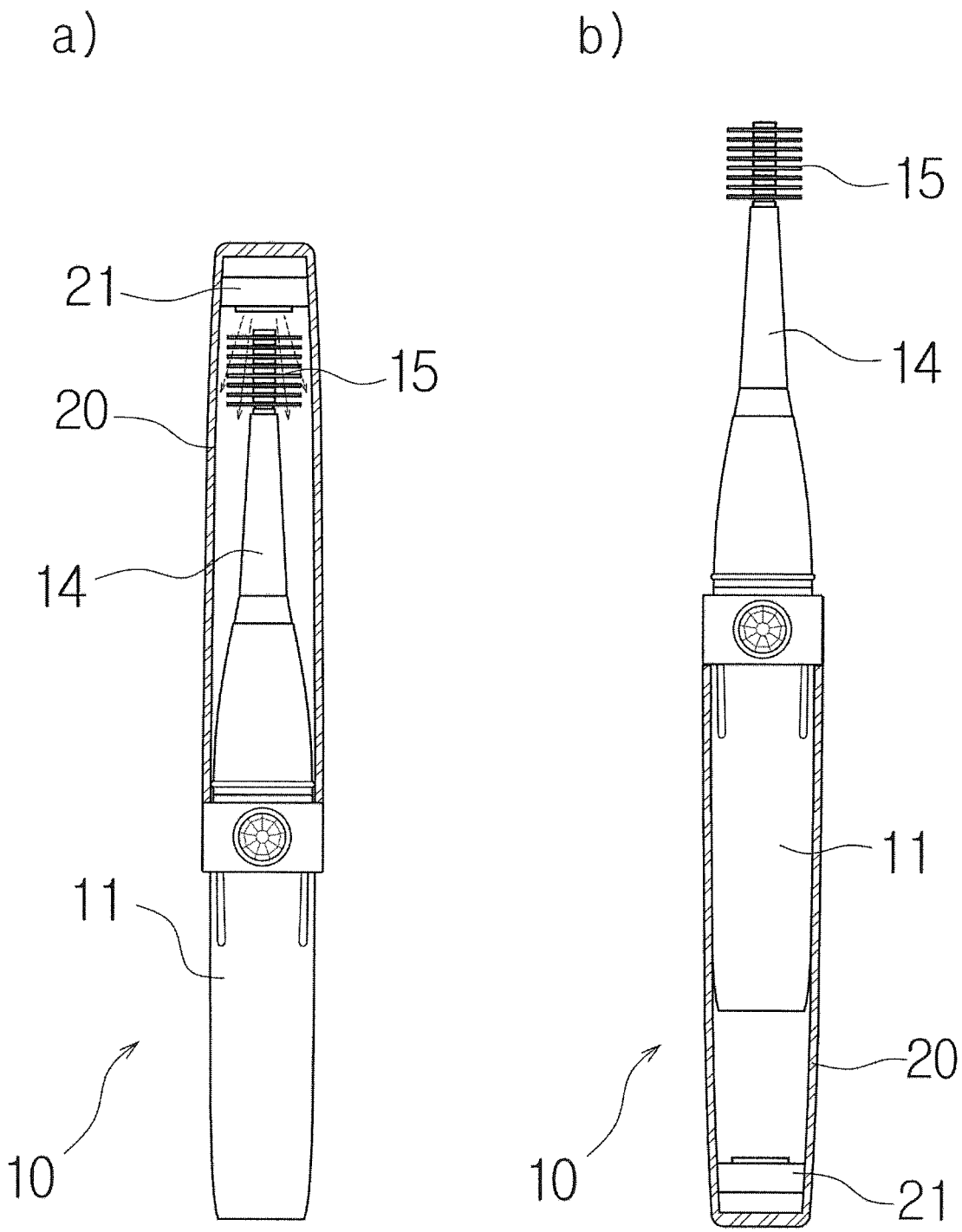
FIG. 9 illustrates configurations and a usage state of another embodiment of the present invention.

In addition, a block cap 20 is preferably further included. As illustrated in a) and b) of FIG. 9, the block cap 20 is, when used, fitted to one side end of the body 11 to extend a length of the handle and, when not used, fitted to the other side of the body 11 to block the shaft 14 and the bristles 15 from the outside. The block cap 20 may include a UV sterilizer 21 provided inside an end portion thereof and configured to, when the block cap 20 is fitted to the body 11, be simultaneously turned on and sterilize a portion around the bristles 15.

As such, as the block cap 20 is fitted to one side end of the body 11 when the vibrating toothbrush 10 of the present invention is used, the length of a portion gripped by a hand is extended, thereby improving convenience for gripping. In addition, as the block cap 20 is fitted to the other side end of the body 11 when the vibrating toothbrush 10 is not used, the bristles 15 is blocked from the outside so that the bristles acting directly inside the mouth and the shaft 14 from being contaminated. Furthermore, as the UV sterilizer 21 is turned on to sterilize the portion around the bristles 15 at the same time when the block cap 20 is fitted to the body 11, sanitation may be maintained after the use of the toothbrush.

Although the disclosure has been described and shown with reference to the embodiment for exemplifying the principle of the disclosure, it is understood that the disclosure should not be limited to the above-described embodiment.

In addition, those skilled in the art can understand that various changes and modifications can be made therein without departing from the subject matters of the disclosure.

Thus, it should be understood that such changes, modifications, and equivalents fall within the spirit and scope of the disclosure.

According to the above embodiments, the present invention has advantageous effects as follows. The exterior of the body 11 is covered by the character outer cover 18 made of a silicon material, and thus, the exterior of the body 11 may be covered by using any of various character outer covers 18, and therefore, a variety of aesthetic appearance may be realized. Also, the outer cover 18 provides a better sense of gripping when a user grips the body 11, and prevents the outer cover 18 from being slipped from the user's hand. In addition, the outer cover 18 prevents vibration generated in the vibration generator 12 from being delivered to the user's hand. Furthermore, the outer cover 18 minimizes the possibility of the vibrating force to be lost in the hand, and transfers the vibrating force to the bristles 15 through the shaft. Moreover, the outer cover 18 prevents water from flowing into the inside.

In addition, according to the present invention, a toothbrushing time is set, for example, to 2 minutes, such that a user is induced to perform toothbrushing for a predetermined period of time, thereby improving use convenience.

In addition, according to the present invention, through sound output in addition to change in vibration generated by the vibration generator 12 and/or turning-on/off operation of light generated by the light source unit 13, a user is allowed to easily check a time to change a toothbrushing region in a multisensory way and change the toothbrushing region, so that the user is able to brush teeth equally.

In addition, according to the present invention, the vibration generator 12 is provided adjacent to a portion of the body 11 in which the light source unit 13 is embedded, and therefore, the vibration generator 12 transfers a vibrating force in the maximum proximity to the shaft 14 to the bristles 15 without any loss of the vibrating force.

In addition, according to the present invention, when the vibration generator 12 is provided on a straight line with the shaft 14, a vibrating force is transferred primarily to the shaft, thereby maximizing the vibrating force. When the vibration generator 12 is provided at a position off the straight line with the shaft 14, vibration. is transferred while a wavelength width of vibration expands as much as a distance from the central axis of the shaft 14.

According to the present invention, the light source unit 13 is provided inside a groove at an end portion on one side of the body 11 from which the shaft 14 is detachable, such that generated light is introduced through one side end of the shaft 14 without a loss and guided to emit light to the outside.

In addition, according to the present invention, a need to change a toothbrushing region may be notified every 30 seconds during a running time for toothbrushing. In doing so, during a toothbrushing operation, tactile alarming is possible through change in vibration generated by a motor, which is the vibration generator 12, and visible alarming is possible through change of a turn-on color or blinking of an LED module which is the light source unit 13. In addition, audible alarming is possible through alarming of a buzzer during a toothbrushing operation. As such, the present invention may integratedly or selectively provide various alarming modes to a user.

In addition, according to the present invention, the vibrating toothbrush 10 may be used with low power consumption using an alarming function for notifying a time to change of a toothbrushing region. As driving power is supplied to the vibration generator 12 and/or the light source unit 13 during an alarming operation time for notifying a time to change a toothbrushing region, it is possible to prevent that a great amount of currents are consumed instantly upon driving of the motor. In addition, as driving currents are not supplied constantly, it is possible to minimize the amount of current consumption, thereby enabling low power-consumption operation compared to the case of supplying currents constantly.

According to the present invention, as the block cap 20 is fitted to one side end of the body 11 when the vibrating toothbrush 10 of the present invention is used, the length of a portion gripped by a hand is extended, thereby improving convenience for gripping. In addition, as the block cap 20 is fitted to the other side end of the body 11 when the vibrating toothbrush 10 is not used, the bristles 15 is blocked from the outside so that the bristles acting directly inside the mouth and the shaft 14 from being contaminated. Furthermore, as the UV sterilizer 21 is turned on to sterilize the portion around the bristles 15 at the same time when the block cap 20 is fitted to the body 11, sanitation may be maintained after the use of the toothbrush.

What is claimed is:

1. A vibrating toothbrush comprising:
   a body defining a handle;
   a vibration generator embedded in the body and configured to generate a vibrating force;
   a light source unit embedded in an end portion on one side of the body and configured to generate light;
   a shaft detachably fixed to the end portion on one side of the body configured to emit the generated light to an outside, guide the generated light to bristles provided on the end portion on one side of the body, and transfer the generated vibrating force to the bristles; and
   a controller provided in the body and configured to perform control to conduct or block power from a power unit to a light source and the vibration generator at every preset cycle during a running time and block power at an operation end point, wherein the controller controls driving currents of the power in a form of pulses in 50% duty cycle for a predetermined alarming operation time during the running time from an operation start point to the operation end point.

2. The vibrating toothbrush of claim 1, wherein an exterior of the body is covered by a water-proof outer cover.

3. The vibrating toothbrush of claim 1, further comprising a sound output unit configured to output sound for an alarming operation time at every preset cycle under control of the controller until a running time expires.

4. The vibrating toothbrush of claim 3, wherein the controller is further configured to conduct power to the vibration generator and the light source unit until expiration of the running time in an manner in which the power is blocked with respect to the vibration generator and the power source unit during an alarming operation time from expiration of each preset cycle and the power is conducted upon expiration of the alarming operation time or in an manner in which the power is conducted to the sound output unit for an alarming operation time and then blocked upon expiration of the alarming operation.

5. The vibrating toothbrush of claim 3,
wherein a running time of the controller is 2 to 3 minutes from an operation start point to the operation end point,
wherein the preset cycle is 30 seconds which is a sum of a main toothbrushing time of 28 seconds for actually performing toothbrushing and an alarming operation time of 2 seconds for notifying a time to change a toothbrushing region, and
wherein a time interval identical to a time interval for the alarming operation is applied to an initial operation start point.

6. The vibrating toothbrush of claim 1,
wherein a running time of the controller is 2 to 3 minutes from an operation start point to the operation end point,
wherein the preset cycle is 30 seconds which is a sum of a main toothbrushing time of 28 seconds for actually performing toothbrushing and an alarming operation time of 2 seconds for notifying a time to change a toothbrushing region, and
wherein a time interval identical to a time interval for the alarming operation is applied to an initial operation start point.

7. The vibrating toothbrush of claim 1, wherein the controller is further configured to:
at an operation start point, conduct the power to the vibration generator and the light source by immediately increasing a level of the power, gradually increasing the level of the power for a predetermined time, or alternatively supplying the power in a pulse form;
at a point of arrival of an alarming operation time upon expiration of each preset cycle, block the power by immediately decreasing the level of the power and, when the alarming operation time expires, conduct the power by the level of the power, gradually increasing the level of the power for the alarming operation time, or alternatively supplying the power in a pulse form; and
at the operation end point, block the power by immediately decreasing the level of the power.

8. The vibrating toothbrush of claim 1, further comprising a block cap which is, when used, fitted to one side end of the body to extend the length of the handle, and, when not used, fitted to the other side end of the body to block the shaft and the bristles from the outside,
wherein the block cap comprises a sterilizer provided inside an end portion thereof and configured to, upon the fitting of the block cap to the body, be turned on simultaneously, thereby sterilizing a portion around the bristles.

* * * * *